United States Patent [19]

Scheele

[11] Patent Number: 5,863,563
[45] Date of Patent: Jan. 26, 1999

[54] TREATMENT OF PULMONARY CONDITIONS ASSOCIATED WITH INSUFFICIENT SECRETION OF SURFACTANT

[75] Inventor: George Scheele, Brookline, Mass.

[73] Assignee: AlphaGene Inc., Charlestown, Mass.

[21] Appl. No.: 326,692

[22] Filed: Oct. 20, 1994

[51] Int. Cl.$^6$ .............................. A61K 9/14; A61K 31/13; A61K 33/00; A61K 33/42

[52] U.S. Cl. ......................... 424/717; 424/489; 424/601; 424/605; 424/606; 514/238.8; 514/255; 514/553; 514/561; 514/578; 514/579; 514/669; 514/826; 514/851; 514/951

[58] Field of Search .................................... 424/400, 489, 424/502, 715, 716, 717, 601, 605, 606; 514/238.8, 255, 553, 561, 578, 579, 669, 826, 851, 951

[56] References Cited

U.S. PATENT DOCUMENTS

| | | | |
|---|---|---|---|
| 2,905,589 | 9/1959 | Miller | 167/58 |
| 4,326,416 | 4/1982 | Fredberg | 73/597 |
| 4,534,343 | 8/1985 | Nowacki et al. | 128/200.23 |
| 4,592,348 | 6/1986 | Waters, IV et al. | 128/200.23 |
| 4,667,668 | 5/1987 | Wetterlin | 128/203.15 |
| 4,814,161 | 3/1989 | Jinks et al. | 424/45 |
| 4,852,561 | 8/1989 | Sperry | 128/200.23 |
| 4,969,473 | 11/1990 | Bothwell | 128/858 |
| 5,230,884 | 7/1993 | Evans et al. | 424/45 |
| 5,279,823 | 1/1994 | Frenz et al. | 424/94.61 |

FOREIGN PATENT DOCUMENTS

WO 93/03709  3/1993  WIPO.
WO 95/24183  9/1995  WIPO.

OTHER PUBLICATIONS

Chander, A., "Regulation of lung surfactant secretion by intracellular pH," American Journal of Physiology, vol. 257, No. 6, part 1 of 3 parts, pp. L354–L360, 1989.

Ruy V. Lourenco, MD et al., "Clinical Aerosols, II. Therapeutic Aerosols," *Arch Intern Med*, 142: 2299–2308, Dec. 1982.

John R. Riordan et al., "Identification of the Cystic Fibrosis Gene: Cloning and Characterization of Complementary DNA," *Science* 245:1066–1072, Sep. 8, 1989.

Bat–Sheva Karem et al., "Identification of the Cystic Fibrosis Gene: Genetic Analysis," *Science* 245:1073–1080, Sep. 8, 1989.

K. Kunzelmann et al., "Bicarbonate permeability of epithelial chloride channels," *Pflügers Arch. Europ. J. of Physiology*, 417, 6/616–621, Feb. 1991.

Jeffrey J. Smith et al., "cAMP Stimulates Bicarbonate Secretion across Normal, but Not cystic Fibrosis Airway Epithelia," *J. Clin. Invest.* 89:1148–1153, Apr. 1992.

Carole M. Liedtke, "Electrolyte transport in the epithelium of pulmonary segments of normal and cystic fibrosis lung," *FASEB* 6, 12:3076–3084, Sep. 1992.

Georges Saumon et al., "Electrolyte and fluid transport across the mature alveolar epithelium," *Journal of Applied Physiology* 74, 1:1–15, Jan. 1993.

George A. Scheele et al., "Role of the GP2/THP Family of GPI–Anchored Proteins in Membrane Trafficking During Regulated Exocrine Secretion," *Pancreas* 9, 2:139–149, 1994.

Henry J. Fuchs, M.D., "Effect of Aerosolized Recombinant Human DNase on Exacerbations of Respiratory Symptoms and on Pulmonary Function in Patients with Cystic Fibrosis," *The New England Journal of Medicine* 331, 10:637–642, Sep. 8, 1994.

Pamela B. Davis, M.D., Ph.D., *The New England Journal of Medicine* 331, 10:672–673, Sep. 8, 1994.

Henrik Verder, M.D. et al., "Surfactant Therapy and Nasal Continuous Positive Airway Pressure for Newborns with Respiratory Distress Syndrome," *The New England Journal of Medicine* 331, 16:1051–1055, Oct. 20, 1994.

P. B'hend et al., "Stimulation of Pancreatic Secretion in Man by Secretin Snuff," *The Lancet*, I, 7802, 509–510, Mar. 10, 1973.

D. Kaiser et al., "Diminished Excretion of Bicarbonate from the Single Sweat Gland of Patients with Cystic Fibrosis of the Pancrease," *Europ. J. Clin. Invest.* 4, 261–265 (1974).

P. R. Durie et al., "Effect of cimetidine and sodium bicarbonate on pancreatic replacement therapy in cystic fibrosis," *Gut*, 778–786, 1980.

Poulsen, Jorgen H. et al., "Bicarbonate conductance and pH regulatory capability of cystic fibrosis transmembrane conductance regulator," Proceedings of the National Academy of Sciences, vol. 91(12), pp. 5340–5344, Jun. 7, 1994.

Lubman, Richard L. et al., "Regulation of intracellular pH in alveolar epithelial cells," Am. J. Physiology, vol. 262(1), part 1 of 2 parts, pp. L1–L14 Jan. 1992.

Medline Abstract 92125483 Jan. 1992.

Bosse, George M., "Nebulized sodium bicarbonate in the treatment of chlorine gas inhalation," Clinical Toxicology, Vo. 32(3), pp. 233–241 1994.

Medline Abstract 94275911, 1994.

Solopov, V.N. et al., "Expectoration Disturbances and Bronchial Obstruction," Respiration, vol. 58(5–6), pp. 287–293, 1991.

Medline Abstract 92:125282, 1991.

(List continued on next page.)

*Primary Examiner*—John Pak
*Attorney, Agent, or Firm*—Fish & Richardson P.C.

[57] ABSTRACT

Methods and compositions for the treatment of the symptoms of a patient who has a pulmonary condition associated with an inhibition of surfactant secretion by type II alveolar cells are described. The method of treatment involves causing a patient to inhale an amount of a pH-raising buffer effective to raise the pH of the aqueous fluid in the microenvironment of the type II alveolar cell lumenal surface, thereby inducing an increase in the rate of surfactant secretion by type II alveolar cells.

36 Claims, 4 Drawing Sheets

OTHER PUBLICATIONS

Scheele, George A. et al., "Pancreatic dysfunction in Cystic fibrosis occurs as a result of impairments in luminal pH, apical trafficking of zymogen granule membranes, and solubilization of secretory enzymes," Pancreas, vol. 12(1), pp. 1–9, 1991.

Medline Abstract 89:130568, 1988.

Solopov, V.N. et al., "Endobronchial therapy in chronic bronchitis patients," Klin. Med., vol. 66(7), pp. 33–36, 1988.

James Baggott, *Textbook of Biochemistry with Clinical Correlations* 1039–1041 and 1049–1052 (Thomas M. Devlin ed., 1992).

Griffiths and Simons, The *trans* Golgi Network: Sorting at the Exit Site of the Golgi Complex, Science 234:438–443, 1986.

Davoust et al., Two Threshold Values of Low pH Block Endocytosis at Different Stages, The EMBO Journal 6:3601–3609, 1987.

Ayala, Transport and Internal Organization of Membranes: Vesicles, Membrane Networks and GTP–binding Proteins, J. Cell Science 107:753–763, 1994.

Gekle and Silbernagl, Comparison of the Buffer Capacity of Endocytotic Vesicles, Lysosomes and Cytoplasm in Cells Derived from the Proximal Tubule of the Kidney, Pflugers Arch—Eur. J. Physiol. 429:452–454, 1995.

TREATMENT OF PULMONARY CONDITIONS ASSOCIATED WITH INSUFFICIENT SECRETION OF SURFACTANT

The field of the invention is treatment of pulmonary symptoms associated with insufficient secretion of surfactant.

BACKGROUND OF THE INVENTION

Efficient gas exchange by the mammalian lung is dependent upon several factors, including the volume and viscosity of the aqueous fluid bathing the lung epithelia. These physical characteristics of the aqueous fluid are dependent upon proper function of alveolar epithelial cells, particularly type II alveolar cells. Type II cells are responsible for secretion of surfactant (a mixture of phospholipids, principally lecithin and sphingomyelin). The surfactant reduces the surface tension of the aqueous fluid bathing the alveoli and contributes to the elastic properties of pulmonary tissue.

Cystic fibrosis is an example of a pulmonary disease associated with the accumulation of thick mucosal secretions which impair alveolar ventilation and $O_2/CO_2$ exchange. Cystic fibrosis is an autosomal recessive genetic disorder characterized by defective fluid secretion in epithelia of the pancreas, small intestine, sweat glands, and airways. The gene to which the defect in cystic fibrosis is attributed encodes a protein which has been characterized as a transmembrane conductance regulator (Riordan et al., Science 245:1066–1072, 1989; Kerem et al., Science 245:1073–1080, 1989). This protein appears to play a role in the functioning of an airway epithelial cell anion channel (Liedtke, FASEB 6:3076–3084, 1992). This anion channel, generally identified as a $Cl^-$ channel, may also act as a channel for secretion of other ions (Smith and Welsh, J. Clin. Invest. 89:1148–1153, 1992; Kunzelmann et al. Pflügers Arch. 417:616–621, 1991).

The pulmonary symptoms of cystic fibrosis and other diseases involving accumulation of thick mucous secretions in the lungs are typically treated with respiratory modalities intended to mobilize the secretions, including regular percussion and postural draining. Various therapeutic aerosols designed to liquefy the mucus or enzymatically digest proteins, nucleic acids, or other mucus components are known in the art (U.S. Pat. No. 2,905,589; U.S. Pat. No. 5,279,823; WO 93/03709; Lourenco and Cotromanes, Arch. Intern. Med. 142:2299–2308, 1982).

SUMMARY OF THE INVENTION

The present invention is based on the discovery that the pulmonary dysfunction characteristic of certain disease states is attributable to the inhibition of secretion of surfactant and other secretory molecules normally produced by type II alveolar cells. This inhibition of secretion is believed to be caused by the uncoupling of endocytosis and exocytosis in these cells, as a result of an abnormally low pH at the apical surface, in the alveolar microenvironment. It is believed that abnormally low pH of the aqueous fluid bathing the apical surface of type II alveolar cells causes a generalized decrease in the normal rate of membrane trafficking within the type II cells. Specifically, an abnormally low pH in the vicinity of the type II alveolar cells causes a defect in the intracellular recycling of exocytic membranes at the apical plasma membrane, a process that normally occurs during apical endocytosis in these cells. Impaired endocytosis results in a generalized defect in the secretory process, including secondary effects which involve a significant decrease in the level of membranes available for exocytosis. Impairment of exocytosis inhibits secretion by type II alveolar cells, in particular secretion of surfactant and other molecules important for pulmonary function. This decrease in secretion of surfactant in turn causes an increase in surface tension of the aqueous film bathing the lumenal aspect of the alveolar space, a decrease in the elastic properties of pulmonary tissue, a concomitant decrease in the rate of gas exchange within the alveolus, and an overall decrease in pulmonary function. An abnormally low pH in the vicinity of the alveolar lumen may also cause a decrease in the solubility of secretory products. As a result, the patient develops a pulmonary disease syndrome, including hampered breathing and inefficient gas exchange.

In general, the invention features a method of treatment of the symptoms of a patient who has a pulmonary condition associated with insufficient secretion of surfactant. More particularly, pulmonary symptoms due to abnormal inhibition of endocytosis (and a concomitant inhibition of exocytosis and surfactant secretion) due to an abnormally low pH in the aqueous fluid bathing the lumenal surface of the type II alveolar cells of the lung are amenable to treatment by the claimed method. The method of treatment involves causing a patient to inhale an amount of a pH-raising buffer effective to raise the pH of the aqueous fluid in the lumenal microenvironment of the type II alveolar cells, thereby inducing an increased level of vesicular membrane trafficking and a concomitant increase in the rate of surfactant secretion by type II alveolar cells. This results in alleviation of the symptoms of the pulmonary condition, and a lessening of pulmonary dysfunction.

Preferably, the amount of the pH-raising buffer inhaled by the patient is sufficient to raise the pH of the aqueous film by an effective amount, e.g. at least 0.1 pH unit, or to a pH value to between about pH 6.1 and about pH 8.5, e.g. about pH 7.0. The target pH is about 6.2 or higher, preferably about 6.4 or higher, more preferably at least about 6.6, even more preferably at least about 6.8, still more preferably about 7.0 or higher, and most preferably about 7.1–8.5 (e.g., about 7.2–8.0). A typical target pH would be pH 7.0, 7.5 or 8.0. The pH-raising buffer may be inhaled as an aerosol of an aqueous solution or as a dry, inhalable powder. Preferably, the pH-raising compound is bicarbonate, although other alkaline buffers may be used.

The invention also features inhalable, dry powder compositions for treatment of the symptoms of a pulmonary condition involving insufficient secretion of surfactant by type II alveolar cells of a patient. The dry powder compositions comprise a pH-raising buffer compound which is present in an amount sufficient to raise the pH of the aqueous fluid bathing the lumenal surface of the type II alveolar cells by at least 0.1 pH unit. At least 50%, and preferably at least 70%, of the composition consists of primary particles of a diameter of 10 μm or less (e.g., between 0.1 and 6 μm). At least 5% by weight (preferably at least 10%, more preferably at least 20%, even more preferably at least 50% and most preferably at least 80% by weight), and up to 100% of the dry powder can consist of the buffer compound, which can be, for example, sodium bicarbonate, potassium bicarbonate, or another alkali metal bicarbonate salt. The particles of the dry powder should be 10 μm or less in diameter at the point of entry of the powder into the respiratory tract of the patient, to maximize deposition of the pH-raising buffer compound in or at the entrance to the lung alveoli. They can, however, be packaged as agglomerates of such primary particles, to be deagglomerated by standard means upon inhalation by the patient from an inhaler designed for that purpose.

A further aspect of the invention is directed to aerosol compositions for treatment of the symptoms of a pulmonary condition involving insufficient secretion of surfactant due to perturbation of lumenal pH and resultant inhibition of membrane trafficking in type II alveolar cells. The aerosol compositions may be composed of an aqueous solution suitable for inhalation consisting of at least 2.5% by weight (more preferably between about 3% and 10% by weight, and most preferably at least about 5% by weight) of a pH-raising buffer compound. The droplets of the aerosol should be 10 µm or less in diameter to maximize deposition in the lung alveoli rather than the throat or upper respiratory tract. Preferably, the buffer compound contains a bicarbonate ion which can be, for example, in the form of sodium bicarbonate, potassium bicarbonate, or another alkali metal bicarbonate salt.

The invention also features inhaler devices for administration of the inhalable compositions (or medicaments) of the subject invention. In one aspect of the invention, the inhaler device comprises a housing defining a chamber which contains a dry powder. The dry powder is composed of a pH-raising buffer compound present in an amount that, upon administration, is effective to raise the pH of the aqueous film bathing the interior surface of the ventilated alveoli of the patient by at least 0.1 pH unit. At least 5% by weight (preferably at least 10%, more preferably at least 20%, even more preferably at least 50%, and up to 100%) of the powder is a pH-raising buffer compound. At least 50% (preferably at least 70%, and more preferably at least 90%) of the powder consists of primary particles which have a diameter of 10 µm or less, and which may be agglomerated into larger particles or agglomerates which readily break down into primary particles upon inhalation from the device. The chamber has an opening through which the medicament can be drawn by inhalation by a patient.

In another aspect of the invention, the inhaler device comprises a vessel containing an inhalable medicament in the form of an aqueous solution suspended in a compressed or liquified propellant gas. At least 2.5% by weight (preferably at least 3%, more preferably at least 4%, even more preferably at least 5% and most preferably between 6 and 10%) of the aqueous solution is a pH-raising buffer compound. The inhaler device also has a housing defining a port onto which the vessel is mounted, a lumen in communication with the port, and a mechanism for controllably releasing the propellant from the vessel into the lumen, thereby releasing the suspended medicament from the vessel into the lumen. The lumen is configured to route the medicament suspended in the propellant into the respiratory system of the patient. At least 50% of the aerosol droplets of the pH-raising medicament delivered by the inhaler are preferably less than 10 µm in diameter.

By "pulmonary condition" is meant a disease which affects lung function. Such conditions may result from a defect in a gene or genes associated with lung function (e.g., cystic fibrosis), asthma, allergies, an immune or autoimmune disorder, a microbial infection (e.g. bacterial, viral, fungal or parasitic infection), or a mechanical injury to the lungs. Particularly of interest is a pulmonary condition associated with insufficient secretion of surfactant by type II alveolar cells as a result of an abnormally low lumenal pH in the vicinity of the type II cells. Such pulmonary conditions may be associated with impairment of normal transport of bicarbonate or other basic ions into the region of the ventilated alveoli. Alternatively, the pulmonary condition may result from the release of acidic components into the lung, as, for example, during degranulation by immune cells in allergic and inflammatory responses. Exemplary pulmonary conditions contemplated by the subject invention include cystic fibrosis, asthmatic bronchitis, tuberculosis, bronchitis, bronchiectasis, laryngotracheobronchitis, bronchiolitis, emphysema, bronchial pneumonia, allergic bronchopneumonia, viral pneumonia, pertussis, diphtheria, spasmodic croup, pulmonary phthisis, encephalitis with retained secretions, and pulmonary edema. Other pulmonary conditions, such as those which develop as a result of injury or surgery (e.g., after tracheotomy), as well as those associated with insufficient surfactant secretion in the lungs of premature infants, are also contemplated by the subject invention. Pulmonary conditions amenable to treatment by the subject method may also develop as a result of activity associated with inhalation of particulate matter [e.g. smoking, exposure to construction areas or other high dust areas, occupational hazards associated with inhalation of particulates, exposure to environmental particulates (e.g. smog, pollen, or asbestos), pulmonary delivery of pharmaceutical agents (e.g. bronchodilators) or inhalation of cocaine].

By "symptoms of a pulmonary condition" is meant symptoms associated with any of the pulmonary conditions described above. The classic symptoms associated with such pulmonary conditions may include coughing, exertional dyspnea, wheezing, chest pain and purulent sputum production. Other components of the syndrome which may accompany a pulmonary condition include hypoxia, $CO_2$ narcosis, hyperventilation, decreased expiration volume, and decreased lung capacity.

By "type II alveolar cells" is meant the cuboidal cells of the alveolus which are responsible for secretion of surfactant.

By "surfactant" is meant the mixture of phospholipids (chiefly lecithin and sphingomyelin), as well as proteins and other as yet undefined components, which is secreted by type II alveolar cells. Surfactant reduces the surface tension of the pulmonary fluids (e.g., the aqueous fluid bathing the alveoli) and contributes to the elastic properties of pulmonary tissue. Type II alveolar cell secretory products such as surfactant are essential for proper lung function.

By "insufficient secretion of surfactant" is meant a level of surfactant secretion which is below the normal level of surfactant secretion. Abnormally low levels of surfactant secretion result in an increase in the surface tension of the aqueous film bathing the lumen of the alveolus, a decrease in the elastic properties of pulmonary tissue, a decrease in the rate of gas exchange, and an overall decrease in pulmonary function.

By "aqueous fluid" or "aqueous film" is meant the pulmonary fluid which bathes the apical surface of the lung epithelium, particularly the alveolar epithelium.

By "abnormally low pH" is meant a pH below the normal pH of the aqueous fluid bathing the lungs, such that the type II alveolar cells have a decreased rate of endocytosis at their apical surface. This results in a decreased rate of membrane recycling within the affected cell, which in turn decreases the rate of exocytosis by the cell. A secondary effect of this cascade is a decreased rate of surfactant secretion. The pH values of human airway liquid tested in tracheotomized normal individuals has been reported to range from pH 6.71 to pH 7.09, while that of patients with various pulmonary conditions ranged from 6.10 to 7.9 (Guerrin et al. 1971 *Prog. Respir. Res.* 6:372–383; herein incorporated by reference).

By "pH in the vicinity of the type II alveolar cells" is meant the pH in the microenvironment of the lumenal surface (i.e. apical plasma membrane), or area immediately surrounding and in contact with the lumenal surface, of type II alveolar cells. The type II alveolar cell microenvironment is the environment at the microscopic or cellular level. The pH in the vicinity of the type II alveolar cells can be determined by measuring the pH of the aqueous fluid bathing the lumenal surface of type II alveolar cells. Alternatively, the existence of normal vs. abnormally low pH in the vicinity of the type II alveolar cell can be determined functionally, by observing lung function before and after treatment with progressively higher doses of the pH-raising buffer of the invention. By "pH-raising buffer", "pH-raising buffer compound", "pH-raising composition", "pH-raising medicament", or "medicament" is meant a composition which, when contacted with a solution (e.g., the aqueous solution bathing the interior of the alveolus), causes a net increase in the solution pH relative to the solution pH prior to addition of the pH-raising buffer. The pH-raising buffer of the invention is effective to raise the pH of the aqueous film at least about 0.1 pH unit.

By "inhaler device" is meant any device useful in the administration of the inhalable medicament of the invention. Examples of inhaler devices include nebulizers, metered dose inhalers, dry powder inhalers, intermittent positive pressure breathing apparatuses, humidifiers, bubble environments, oxygen chambers, oxygen masks and artificial respirators.

DESCRIPTION OF THE PREFERRED EMBODIMENTS

The method and compositions encompassed by the subject invention may be used in the treatment of pulmonary disease which may result from an inhibition of surfactant secretion associated with an abnormally low (acidic) pH in the alveolar microenvironment. The subject invention treats these conditions by effecting an increase in the pH of the aqueous fluid bathing the lumenal surface of the ventilated alveoli, particularly in the vicinity of the type II alveolar cells. This is achieved by causing the patient to inhale a composition containing a pH-raising buffer compound.

pH-raising buffer compounds

The pH-raising buffer compound may be any physiologically compatible buffer compound or mixture of compounds effective in increasing the pH of the aqueous fluid in the vicinity of the lumenal surface of type II alveolar cells. Exemplary pH-raising buffers include alkali metal salts of bicarbonate, BIS-TRIS propane, BES, MOPS, TES, HEPES, DIPSO, TAPSO, TRIZMA, HEPPSO, POPSO, EPPS, TEA, Tricine, Bicine, CAPS, TAPS, dibasic sodium phosphate, dibasic potassium phosphate, and triethanolamine (all available from Sigma Chemical Company, St. Louis, Mis.); also useful would be any suitable biologically-compatable, alkaline-adjusted buffer having an appropriate pH. Preferably, the pH-raising buffer contains bicarbonate ion. The bicarbonate ion is present in the composition as an alkali metal salt, preferably as sodium bicarbonate or potassium bicarbonate, or as a mixture of sodium bicarbonate and potassium bicarbonate. Where the patient to be treated suffers from multisystem disease, high blood pressure, or heart disease; is at risk of heart failure; or suffers from other conditions for which exposure to sodium ions is contraindicated, use of potassium bicarbonate alone or a mixture of sodium bicarbonate and potassium bicarbonate is preferred.

Formulations

The pH-raising buffer compositions of the subject invention may be prepared either as a dry, inhalable powder or as an aerosol of an aqueous solution.

Where the pH-raising composition is a dry powder, at least 5% by weight (preferably at least 10%, more preferably at least 20%, and even more preferably at least 50%, and up to 100%) of the powder consists of a pH-raising buffer compound. The dry powder composition is prepared by standard methods, including micronizing to produce primary particles of the proper size (preferably less than 10 $\mu$m in diameter). The dry powder may be entirely made up of the buffer compound, or may be a mixture of the buffer compound and a diluent suitable for inhalation, such as lactose, maltose, or other physiologically acceptable compound recognized in the art as useful as a dry powder diluent for inhalation.

Where the pH-raising composition is an aerosol of an aqueous solution, more than 2% by weight, normally at least 2.5% by weight, preferably between about 3% and 10% by weight, more preferably at least about 5% by weight of the solution consists of the pH-raising buffer compound. Where the pH-raising buffer compound contains bicarbonate ion, the concentration of the bicarbonate ion in the aqueous solution is preferably between about 0.25M and 1.0M.

The composition for administration may be prepared by mixing the selected pH-raising compound in an appropriate diluent (e.g. a dry powder diluent or aqueous diluent) by methods well known in the art. For example, the aqueous solution is prepared by dissolving the pH-raising compound in an appropriate volume of water; physiological saline, ½ concentration physiological saline; or other suitable, physiologically acceptable vehicle. The solution is then filtered, placed in a closed container, and sterilized (e.g. by autoclaving at 121° C. for fifteen minutes).

Where the composition is to be administered as a dry powder, the pH-raising buffer compound is micronized, preferably so as to be composed of particles of less than 10 $\mu$m in diameter. The micronized pH-raising buffer compound may then be mixed with a dry powder diluent, such as lactose, to provide an appropriate concentration of the pH-raising buffer compound. The mixture is optionally encapsulated by methods known in the art. The capsules constitute a convenient means for administering a single inhalation dosage of the pH-raising compound, similar to the capsules employed in a ROTOHALER™ dry powder inhaler device.

As will be appreciated by one of skill in the art, the pH-raising formulations described herein may contain components in addition to a pH-raising buffer compound and optional diluent. For example, the composition may also contain penetrating and surface wetting agents (e.g. alkylaryl polyether alcohols, including oxyethylated alkylphenolformaldehyde polymers), droplet stabilizing agents (e.g. glycerol, propylene glycol or similar polyhydroxy alcohol), antifoaming agents (e.g. silicone), dispersing agents (e.g. oleic acid, sorbitan trioleate, soya lecithin), propellants (trichloromonofluoromethane, dichlorodifluoromethane, dichlorotetrafluoroethane), flavoring agents and/or other agents which may be commonly used in the preparation of inhalable dry powder or aerosol medicaments. The pH-raising formulations of the subject invention may also contain respiratory therapeutic agents known in the art (e.g. artificial surfactants, antimicrobials, anti-inflammatory compounds, or nucleases). Alternatively, the method of treatment of the subject invention may be practiced in combination with respiratory therapies known in the art.

Determination of the preferred propellant, design of the inhaler, and formulation of the pH-raising buffer compound in its carrier are well within the abilities of those of ordinary skill in the art of devising routine inhalation therapies. The portable inhaler may contain a canister containing an aerosol formulation of a pH-raising buffer compound, preferably in a propellant such as a chlorofluorocarbon or any alternative means of providing an aerosol of a pH-raising buffer compound. Alternatively, or in addition, the inhaler may contain a pH-raising buffer compound either mixed in dry form with a propellant or held in a chamber separate from the propellant, or mixed with a liquid carrier capable of being nebulized to an appropriate droplet size, or in any other configuration known to those skilled in inhaler technology. A few of the several types of inhaler designs that have been developed to date are discussed in, for example, U.S. Pat. Nos. 4,667,668; 4,592,348; 4,534,343; and 4,852,561, each of which patents is herein incorporated by reference. Other inhaler designs are described in the *Physicians' Desk Reference*, 47th Edition, Edward R. Barnhart, Publisher (1993). Each of these and other aerosol-type inhalers can be adapted to accommodate the delivery of pH-raising buffer compounds. Also useful for delivering a pH-raising buffer compound formulated in dry powder form is a non-aerosol-type inhaler device such as the ROTOHALER®, SPINHALER®, TURBUHALER®, and MONOHALER® devices.

Inhalation Devices

Figure 1:
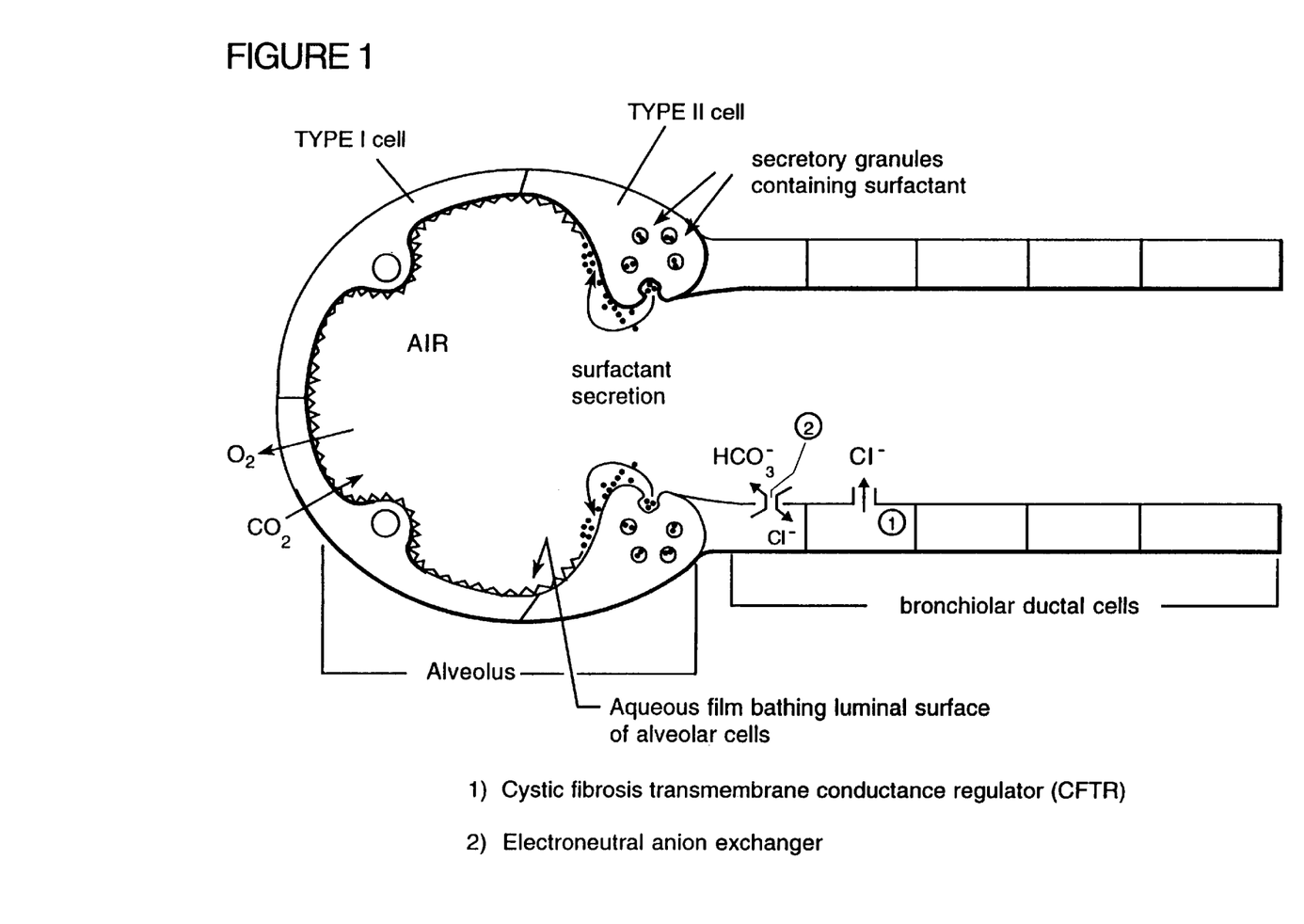
FIG. 1 is a schematic diagram of a human alveolus. Normal chloride transport (for example, via the cystic fibrosis transmembrane conductance regulator); chloride/bicarbonate exchange (for example, via the electroneutral anion exchanger); exocytosis of secretory granules by type II alveolar cells (which secrete surfactant); and $CO_2/O_2$ exchange across type I alveolar cell membranes are depicted.
Figure 2:
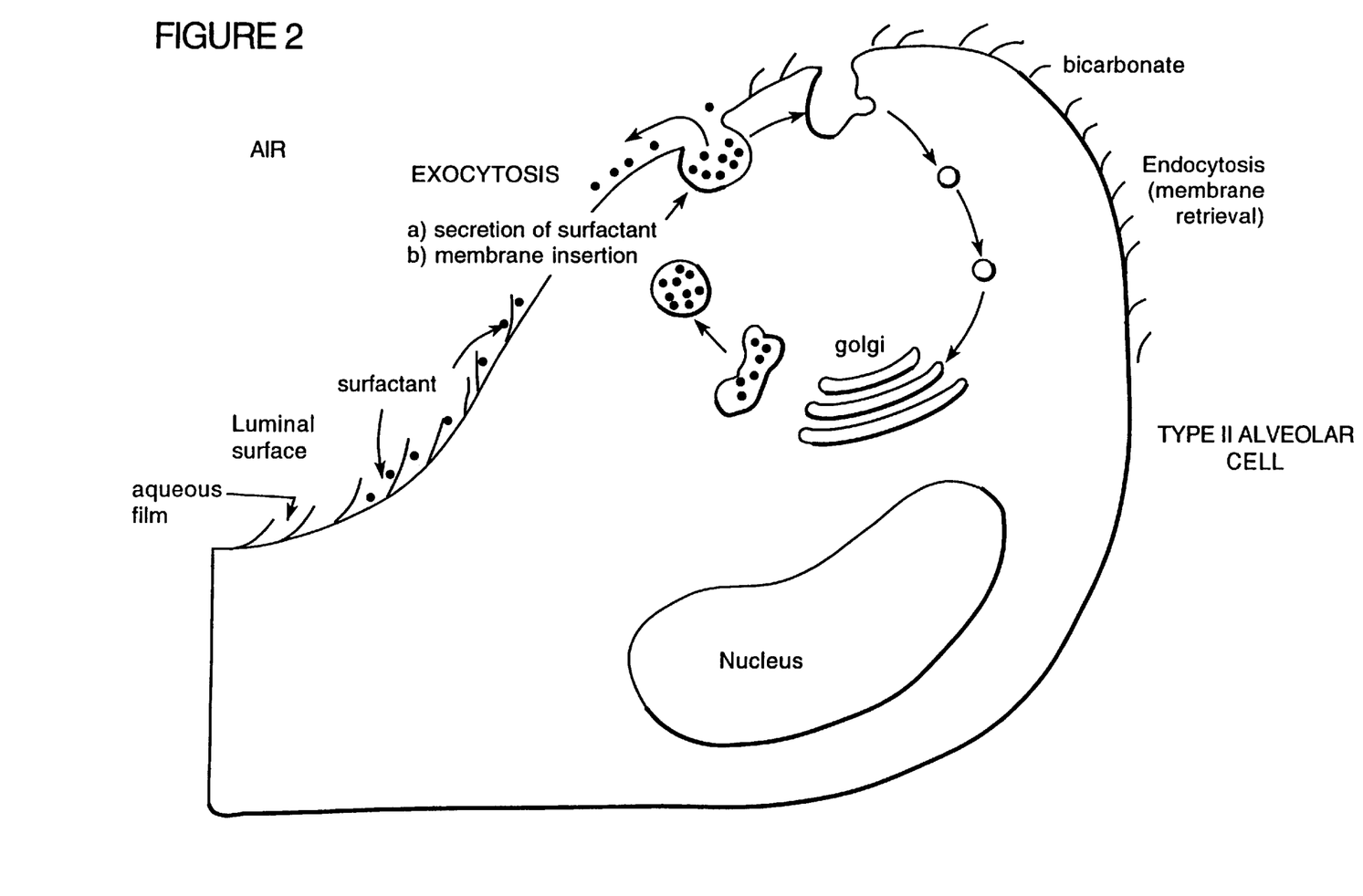
FIG. 2 is a schematic diagram of a type II alveolar cell. The normal cyclic process of pH-dependent membrane trafficking (endocytosis and exocytosis) is depicted.
Figure 3:
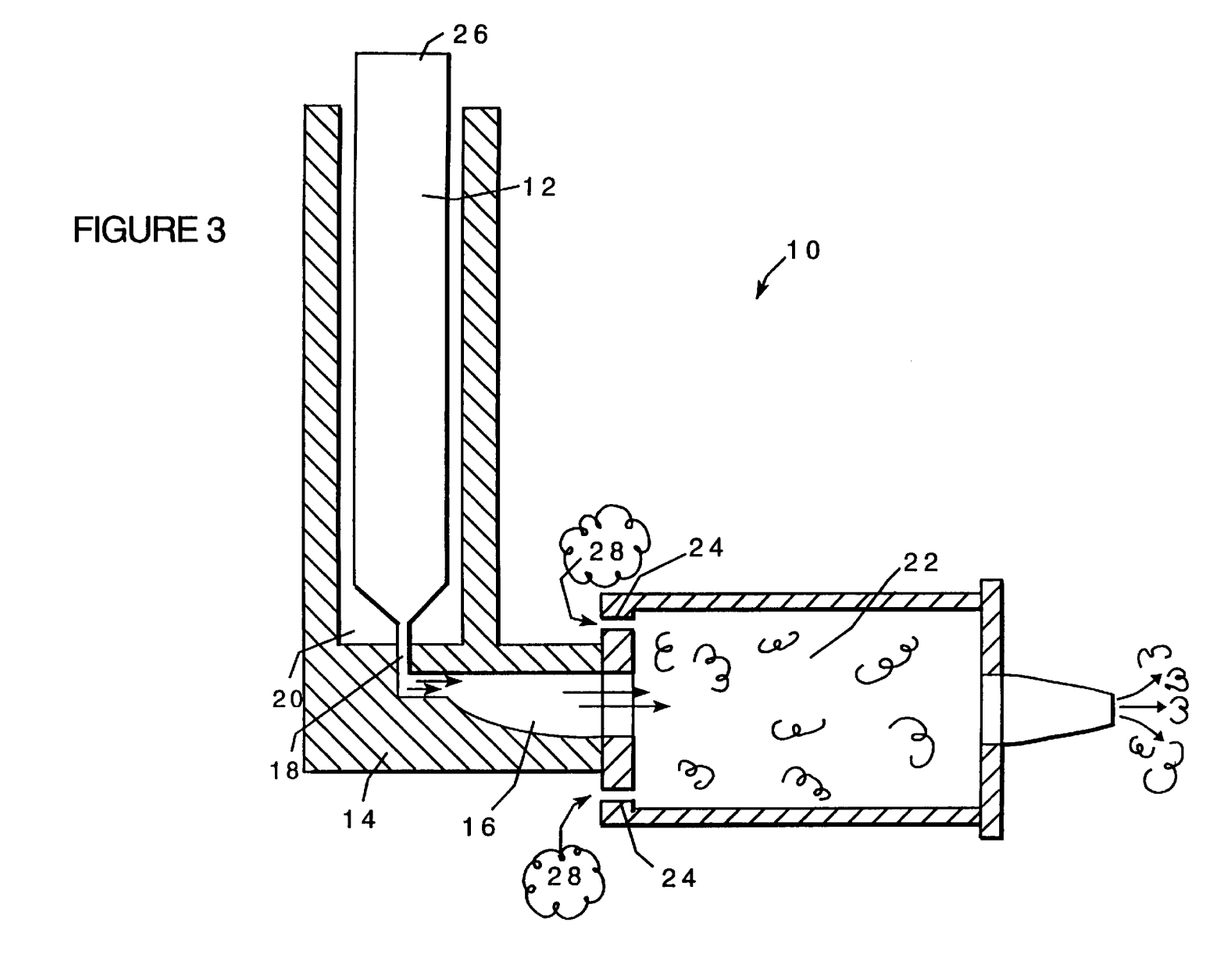
FIG. 3 is a diagram of an exemplary inhaler device suitable for delivery of a pH-raising buffer composition of the invention formulated as an aerosolized solution.

An exemplary inhaler device 10 for administration of the inhalation therapy of the invention is illustrated in cross-section in FIG. 3, which shows a housing 14 defining a chamber 20 in communication with a lumen 16 via a port 30; a vessel 12 containing pressurized gas having at least 2.5% by weight of a pH-raising buffer compound dissolved in a liquified propellant or compressed inert gas, and/or which contains a suspension of a solid or liquid pH-raising buffer compound, which vessel 12 is slidably mounted in the chamber 20; a port 30 onto which the vessel 12 is mounted, and which is in communication with the lumen 16; a pressure-activated valve mechanism 18 for controllably releasing the pressurized contents of the vessel 12 into the lumen 16; and, constituting one end of the lumen 16, a rebreathing chamber 22 having one-way valves 24 through which air 28 can enter the rebreathing chamber 22, but through which the contents of the rebreathing chamber 22 cannot escape. A patient utilizes the device by pushing the upper end 26 of the vessel 12 which protrudes from the housing 14, thereby sliding the vessel 12 down into the chamber 20 and depressing the valve mechanism 18. This causes the pressurized contents of the vessel 12 to be released into the lumen 16 and the rebreathing chamber 22. The patient then inhales a portion of the contents of the rebreathing chamber 22, drawing air 28 through the one-way valve 24 into the rebreathing chamber 22 to replace the portion of the contents inhaled by the patient. A single dose of the therapeutic agent released from the vessel 12 into the rebreathing chamber 22 may take several breaths to be sufficiently inhaled by the patient. The total weight of this device would be less than 200 grams, so that it is readily portable.

Figure 4:
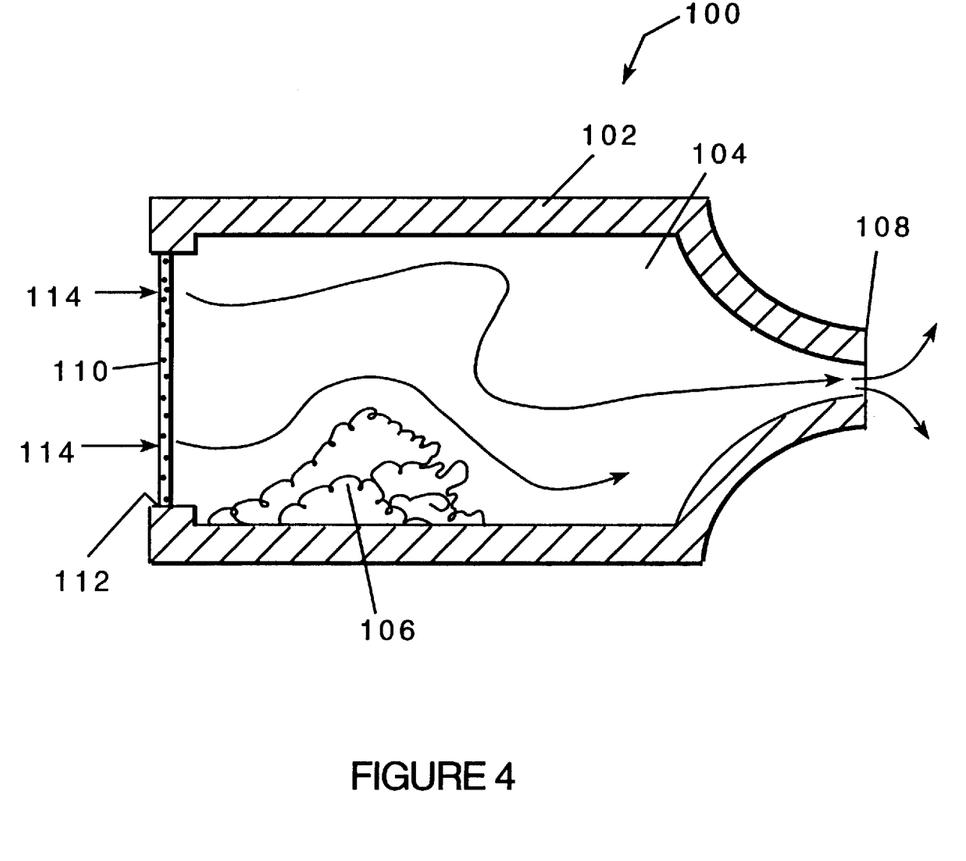
FIG. 4 is a diagram of an exemplary inhaler device suitable for delivery of a pH-raising buffer composition of the invention formulated as an inhalable dry powder.

Another exemplary inhaler device 100, illustrated in FIG. 4, is a breath-actuated dry powder inhaler for use in administering the pH-raising buffer compound of the invention, formulated as an inhalable dry powder. The housing 102 defines a chamber 104 containing a dose of a pH-raising buffer compound formulated as an inhalable dry powder 106, and having an open mouthpiece end 108 in communication with the chamber 104. At the end of the housing 102 opposite the open mouthpiece end 108, a section of air-permeable material 110 covers an opening 112 in the housing 102. Air 114 can be readily drawn into the chamber 104 through the air permeable material 110 covering the opening 112, but the powder 106 cannot exit the device through the opening 112. The patient inhales by mouth through the open mouthpiece end 108, thereby forcing air 114 through the section of air-permeable material 110 covering the opening 112, and into the chamber 104. The movement of the air 114 within the chamber 104 results in suspension of the powder 106 in the moving air 114 and subsequent inhalation of the powder 106 with the inspired air 114.

Identification of patients

Any patient presenting with the symptoms of a pulmonary condition associated with insufficient secretion of surfactant as a result of an abnormally low pH in the vicinity of the lumenal surface of type II alveolar cells may be treated by the method of the subject invention. The low pH of the aqueous fluid may result from a genetic disorder (e.g. a defect in a protein responsible for ion transport), an immunological reaction (e.g. asthma), a microbial infection, or a mechanical injury to the lung (e.g. resulting from surgery).

Specific pulmonary diseases which may be treated by the method of the subject invention include cystic fibrosis, asthmatic bronchitis, tuberculosis, bronchitis, bronchiectasis, laryngotracheobronchitis, bronchiolitis, emphysema, bronchial pneumonia, allergic bronchopneumonia, viral pneumonia, pertussis, diphtheria, spasmodic croup, pulmonary phthisis, encephalitis with retained secretions, and pulmonary edema. An example of a mechanical injury (e.g. resulting from surgery) which may lead to a pulmonary condition treatable in accordance with the invention is the injury which results from a tracheotomy. Pulmonary conditions associated with insufficient surfactant secretion in the lungs of premature infants may also be treated by the subject method. Other pulmonary conditions which are amenable to treatment include those which result from prolonged artificial (i.e., mechanical) respiration, from smoking, or from inhalation of particulate matter, such as inhalation of dust or asbestos particles. Pulmonary conditions which result from breathing in environments high in particulate matter (e.g. smog, pollen, dust) are also amenable to treatment by the method of the subject invention. Preferably, the disease to be treated is cystic fibrosis.

Where the precise diagnosis of the pulmonary condition is uncertain, or where it is uncertain if the diagnosed pulmonary condition is associated with an abnormally low pH of the aqueous fluid in the vicinity of the lumenal surface of type II alveolar cells, the pH of the mucosal secretions of the lungs may be tested by methods well known in the art. For example, the pH of aqueous fluid in the vicinity of the lumenal surface of type II alveolar cells may be approximated by testing the pH of patient sputum. The sputum may be dissolved or suspended in an appropriate volume of water and the pH tested with a pH meter or a pH test strip. The pH may also be determined by determining the pH of a sample of fluid obtained by bronchoscopy or pulmonary lavage (including broncho-alveolar lavage, bronchial brushings, and mucosal biopsy). Samples for pH testing may also be obtained by percutaneous needle biopsy and aspiration.

Alternatively, the patient with an undetermined pulmonary condition can be treated by the method of the invention, which is relatively benign. Changes in pulmonary function can be monitored as a function of time after and during treatment in order to determine whether the method results in an improvement in pulmonary function. Pulmonary function can be monitored by a variety of tests well known in the art, including tests for lung capacity. The fact that the patient's pulmonary function improves with treatment in accordance with the invention is a strong indication that the patient's pre-treatment pulmonary condition was attributable to low pH in the vicinity of the patient's type II alveolar cells.

Timing of administration

The pH-raising compositions may be administered at any stage of the patient's pulmonary disease. Patients most likely to benefit from the therapy of the subject invention are those who are in an early stage of disease, i.e., their airways are not so blocked that the pH-raising compositions cannot reach the alveoli. Preferably, therapy is initiated at the earliest signs of pulmonary symptoms so as to avoid secondary complications (e.g. bacterial or viral infections) associated with the accumulation of thick mucosal secretions.

The pH-raising compositions may be administered for any period over which treatment is necessary, and may be adjusted according to the particular pulmonary condition of the patient. For example, if the patient suffers from asthma, the compositions may be administered as needed to aid in the relief of an acute attack. Alternatively, administration of the pH-raising compositions may be long-term, e.g. daily (one or more times a day) for several weeks to several months or even years. Therapy may be continued so as to maintain the pH of the aqueous fluid bathing the alveoli for the life of the patient or until the patient is no longer susceptible to pulmonary disease. The pH-raising compositions may be administered in conjunction with other therapeutic compounds (e.g., bronchodilators or antimicrobials) as needed.

The therapeutic method of the invention may also be employed as a prophylactic measure to prevent the development of pulmonary disease in susceptible patients. For example, individuals who have been diagnosed with cystic fibrosis, but have not yet developed the severe, chronic pulmonary symptoms associated with the disease, may be prophylactically treated with the pH-raising compositions described herein. Other individuals who may benefit from prophylactic therapy include tobacco smokers, cocaine users, individuals susceptible to allergic asthma (e.g. asthma associated with inhalation of pollen), individuals susceptible to asbestosis, and workers exposed to high dust or high particulate environments (e.g. occupational hazards). In general, individuals which engage in activity that may compromise lung function through deposition of particulate matter in the lungs can benefit from prophylactic treatment by the method of the invention.

Deposition of particulate matter in the lungs can inhibit normal ion secretion into the epithelial airway, resulting in an abnormally low pH in the type II cell microenvironment, a concomitant decrease in type II cell endocytosis which results in a decrease in surfactant secretion, and ultimately loss of normal pulmonary function. Alternatively, deposition of particulate matter in the lungs may cause inflammation of the airways. Pulmonary inflammation is associated with the release of acidic components during immune cell degranulation. The acidic components can then effect a decrease in the pH of the aqueous fluid bathing the lungs, eventually resulting in loss of normal pulmonary function as described above.

Method of administration

The pH-raising compositions are administered directly to the lungs of the patient, preferably by causing the patient to inhale the compositions. Delivery to the alveoli is achieved by causing the patient to inhale an inhalable, dry powder composition or an aerosol composition as described above. This may be accomplished by isolating the patient (e.g. in an oxygen tent or an incubator), humidifying the isolated environment, and introducing the medicament of the subject invention into the humidified environment, e.g. by dripping the fluid into a nebulizer. Alternatively, the compositions may be administered with a portable (e.g. hand-held) nebulizer, a metered-dose inhaler (MDI), a dry powder inhaler, or other inhaler device known in the art. In general, nebulizers are devices which have a mechanical or electronic means to generate and deliver a fine mist of a liquid medicament. MDIs typically comprise a canister under pressure fitted with a metering valve. The canister is filled with an aerosol formulation that includes the medicament dissolved or dispersed in a compressed or liquified propellant gas. Exemplary propellants which may be used in the subject invention are described in, for example, U.S. Pat. No. 4,814,161, and are well known in the art. Nebulizers, MDIs, and dry powder inhalers useful for administration of the pH-raising compounds of the invention are also well known in the art.

Where the pH-raising composition is in the form of a dry, inhalable powder, the composition will preferably be administered with an inhaler device which has a housing which defines a chamber containing the inhalable, pH-raising medicament, or into which the medicament can be readily introduced, and an opening through which the medicament can be drawn by inhalation by the patient. The inhaler is capable of delivering the dry powder such that at least 50% of the dry powder is in the form of primary particles less than 10 $\mu$m in diameter. The primary particles optionally may be agglomerated into larger particles which readily break down into primary particles of the desired size upon inhalation from the device. Exemplary dry powder inhalers which may be used for delivery of the inhalable, dry powder formulation of the pH-raising medicament include the commercially available SPINHALER™, ROTOHALER™ and TURBUHALER™ dry powder inhalers. The device can be designed to deliver a single dose of from about 10 $\mu$g to 100 mg, preferably 50 $\mu$g to 10 mg, more preferably 100 $\mu$g to 5 mg of the pH-raising compound.

Where the pH-raising composition is in the form of an aerosol, the composition will preferably be administered with an inhaler device suitable for delivery of an aerosol (e.g. MDI, nebulizer) which has a vessel containing the pH-raising composition suspended in a compressed or liquified propellant gas. The housing of the inhaler device defines a port onto which the vessel is mounted, a lumen which communicates with the port, and a mechanism for controllably releasing the propellant from the vessel into the lumen, thereby releasing the suspended pH-raising composition from the vessel into the lumen. The lumen is configured to route the delivery of the pH-raising composition into the respiratory system of the patient. The inhaler is preferably capable of delivering the aerosol in the form of droplets which are less than 10 μm in diameter. The device can be designed to deliver a single dose or multiple doses, each of which contains about 10 μg to 100 mg, preferably 50 μg to 10 mg, more preferably 100 μg to 5 mg by weight of the pH-raising compound.

In general, when using an inhaler device to administer the pH-raising medicament, the patient first exhales, so as to evacuate the air from his or her lungs as completely as possible. As the patient inhales, the inhaler device is either manually or electronically activated to produce a fine mist of the pH-raising medicament. The pH-raising medicament is then carried into the lungs with the inspiratory air and delivered to the alveoli.

Preferably, the inhaler device used is capable of generating a fine mist of the pH-raising medicament so as to maximize the deposition of the pH-raising buffer compound in the alveoli. Some of the medicament will, of course, be deposited in other parts of the respiratory tract prior to reaching the alveoli, but use of particles or droplets of diameter less than 10 μm will minimize this loss. Preferably, where the pH-raising composition is in the form of a dry powder, at least 50% (by weight) of the powder consists of particles less than 10 μm in diameter at the point where the powder enters the respiratory tract. Where the pH-raising composition is in the form of an aerosol of an aqueous solution of the pH-raising buffer compound, at least 50% (by weight) of the aerosol droplets are 10 μm or less in diameter. Preferably, the particle or droplet size of the pH-raising medicament is between about 0.1 and 6 μm. Although particles or droplets larger than 10 μm in diameter may be used to administer the pH-raising compositions of the subject invention, alveolar delivery of the pH-raising buffer compound will be less efficient due to the deposition of the particles or droplets in the non-alveolar areas of the respiratory tract, such as the back of the throat or the bronchi.

An effective dosage of the pH-raising buffer compound inhaled by the patient is the amount of the pH-raising buffer compound effective to cause an increase in the rate of surfactant secretion by type II alveolar cells in the ventilated alveoli of the patient. Preferably, the amount of the pH-raising buffer compound inhaled is that amount sufficient to raise by at least 0.1 pH unit, more preferably by at least 0.2 pH unit, even more preferably by at least 0.5 pH unit, up to about 1.0 pH unit or more, the pH of the aqueous film bathing the lumenal surface of the ventilated alveoli, and more preferably to raise the pH value of the aqueous film to a level above pH 6.1, such as pH 7.0. If pH 7.0 is insufficiently high to accomplish the therapeutic aim of the invention, then additional pH-raising buffer can be administered to raise the pH to 7.5, 8.0, 8.5, or even 9.0.

The pH associated with optimal lung function, and the dosage necessary to achieve it, may vary from patient to patient. Also, these factors may vary under different pathophysiological conditions. It is therefore expected that the optimal dose for a given patient will need to be determined empirically, by testing various dosage levels. This can be readily accomplished using the methods described herein. For example, appropriate dosages of the pH-raising buffer compound can be determined by calculating the approximate surface area of the patient's lung, the volume of the aqueous fluid bathing the lung epithelium, and an amount of a pH-raising buffer compound effective to increase the pH of this volume of aqueous fluid by a desired number of pH units.

Individuals receiving the therapy of the subject invention, including both those individuals diagnosed with a pulmonary condition as well as those individuals susceptible to development of a pulmonary condition (and thus candidates for prophylactic therapy), may receive the inhalation treatment as a discrete, single dose administered at least once per day, e.g. 1 to 12 times a day, preferably 2 to 8 times a day. Alternatively, the treatment can be continuous over periods of, for example, one to ten minutes duration, repeated every hour or every few hours, as needed. The extent of treatment is dictated by the patient's condition, there being no inherent limitation on the frequency or duration of treatment by the method of the invention. Continuous administration overnight or even 24 hours per day can be accomplished by incorporating a mist or powder containing the therapeutic of the invention into the air delivered by, for example, oxygen mask, mechanical respirator, or humidifier, or that supplied in an enclosed environment (e.g., isolation chamber such as an oxygen tent or incubator). Total dosages of the pH-raising buffer compound over a 24 hour period may range from microgram or milligram amounts, up to gram amounts (e.g. about 5 g to 50 g). Appropriate dosages are dependent upon the particular individual being treated (e.g. patient size, lung capacity, disease severity), and can be varied accordingly.

The dosage of the pH-raising buffer composition may be adjusted according to the needs of the individual patient. For example, where the pH of the mucosal secretions has not increased sufficiently after a given dose, as determined by the pH test described above or as evidenced by continued pulmonary dysfunction, the dosage of the pH-raising buffer composition may be increased. Methods for testing the pH of lung secretions (e.g. testing pH of sputum samples or sample obtained by bronchoscopy or pulmonary lavage) are described above and are well known in the art. Alternatively, patients receiving the therapy of the subject invention may be monitored by pulmonary function tests (e.g. tests for lung capacity, $pO_2$ and $pCO_2$, and tests for arterial blood gasses) which are well known in the art. Normal values of arterial $CO_2$ partial pressure ($P_{aCO2}$) range from 35 to 45 mm Hg, while normal values of arterial $O_2$ partial pressure ($P_{aO2}$) range from 75 to 100 mm Hg. Normal $P_{aO2}$ varies with age and may be calculated by the following formula: $P_{aO2}$=104−[0.27×age in years]. Normal lung ventilation is about 14 breaths per min, with a tidal volume of 400 ml per breath and a ventilation rate of 5.6 liters per minute.

Lung capacity may be tested by normal means well known in the art, including the use of a spirometer. The normal ratio of the forced expiratory volume in the first second of expiration ($FEV_1$) to the forced vital capacity (FVC) is $FEV_1/FVC \geq 2$ liters (males). Other measures of pulmonary function include measurement of lung elasticity, which assesses the measurement of static transpulmonary pressure as a function of lung volume. Normal values for static compliance range from 0.1 to 0.4 l/cm $H_2O$. Pulmonary function may also be assessed by exercise testing and various imaging techniques, including X-radiography and ventilation scan (using radioactive gases). An additional example of a device useful in determining lung capacity is the acoustic pulse response measuring device described in U.S. Pat. No. 4,326,416, herein incorporated by reference.

Thus the patient may be followed throughout therapy, as well as after therapy, to determine the need for an increased dosage of the medicament, the need to re-initiate therapy, and/or the efficacy of therapy for that particular patient. The pH-raising buffer may be administered by a physician in a hospital setting (e.g. where artificial respiration is required) or may be self-administered.

Other embodiments are within the following claims.

What is claimed is:

1. A method for treating the symptoms of a pulmonary condition involving insufficient secretion of surfactant by type II alveolar cells, said insufficiency being attributable to abnormally low pH of the aqueous film bathing the alveolar luminal surface of said cells, said method comprising causing a patient suspected of having said pulmonary condition to inhale an amount of a pH-raising buffer effective to alleviate said symptoms, wherein (1) the buffer is provided to the patient in the form of a powder, and (2) said pulmonary condition is selected from the group consisting of cystic fibrosis, pulmonary edema, bronchiectasis, bronchiolitis, emphysema, bronchial pneumonia, allergic bronchopneumonia, viral pneumonia, and encephalitis with retained secretions.

2. The method of claim 1, wherein at the point said powder enters the respiratory tract of said patient, at least 50% by weight of the powder consists of particles less than 10 $\mu$m in diameter.

3. The method of claim 1, wherein said buffer comprises bicarbonate ion.

4. The method of claim 1, wherein said buffer comprises sodium bicarbonate or potassium bicarbonate.

5. The method of claim 1, wherein said buffer comprises BIS-TRIS propane, MOPS, HEPES, DIPSO, TAPSO, TRIZMA, HEPPSO, POPSO, EPPS, Tricine, Bicine, CAPS, dibasic sodium phosphate, dibasic potassium phosphate, or triethanolamine.

6. The method of claim 1, wherein the pulmonary condition is cystic fibrosis.

7. The method of claim 4, wherein the pulmonary condition is cystic fibrosis.

8. A method for treating the symptoms of a pulmonary condition involving insufficient secretion of surfactant by type II alveolar cells, said insufficiency being attributable to abnormally low pH of the aqueous film bathing the alveolar luminal surface of said cells, said method comprising causing a patient suspected of having said pulmonary condition to inhale an amount of a pH-raising buffer effective to alleviate said symptoms, wherein (1) the buffer is provided to the patient in the form of a solution that does not contain an alkyl aryl polyether alcohol, and (2) said pulmonary condition is selected from the group consisting of cystic fibrosis, pulmonary edema, bronchiectasis, bronchiolitis, emphysema, bronchial pneumonia, allergic bronchopneumonia, viral pneumonia, and encephalitis with retained secretions.

9. The method of claim 8, wherein said buffer comprises bicarbonate ion.

10. The method of claim 8, wherein said buffer comprises BIS-TRIS propane, MOPS, HEPES, DIPSO, TAPSO, TRIZMA, HEPPSO, POPSO, EPPS, Tricine, Bicine, CAPS, dibasic sodium phosphate, dibasic potassium phosphate, or triethanolamine.

11. The method of claim 8, wherein said buffer comprises sodium bicarbonate or potassium bicarbonate.

12. The method of claim 8, wherein the pulmonary condition is cystic fibrosis.

13. A method for treating the symptoms of a pulmonary condition involving insufficient secretion of surfactant by type II alveolar cells, said insufficiency being attributable to abnormally low pH of the aqueous film bathing the alveolar luminal surface of said cells, said method comprising causing a patient suspected of having said pulmonary condition to inhale an amount of a pH-raising buffer effective to alleviate said symptoms, wherein (1) the buffer is provided to the patient in the form of a solution that, if the buffer is an alkali metal bicarbonate, contains at least 2.5% said buffer by weight; and (2) said pulmonary condition i s selected from the group consisting of cystic fibrosis, pulmonary edema, bronchiectasis, bronchiolitis, emphysema, bronchial pneumonia, allergic bronchopneumonia, viral pneumonia, and encephalitis with retained secretions.

14. The method of claim 13, wherein said buffer comprises bicarbonate ion.

15. The method of claim 13, wherein said buffer comprises DIS-TRIS propane, MOPS, HEPES, DIPSO, TAPSO, TRIZMA, HEPPSO, POPSO, EPPS, Tricine, Bicine, CAPS, dibasic sodium phosphate, dibasic potassium phosphate, or triethanolamine.

16. The method of claim 13, wherein the pulmonary condition is cystic fibrosis.

17. The method of claim 14, wherein the pulmonary condition is cystic fibrosis.

18. A method for treatment of an individual susceptible to a pulmonary condition involving insufficient secretion of surfactant by type II alveolar cells, said insufficiency being attributable to abnormally low pH of the aqueous film bathing the alveolar luminal surface of said cells, said method comprising causing an individual susceptible to said pulmonary condition to inhale an amount of a pH-raising buffer effective to maintain a normal rate of surfactant secretion by type II alveolar cells in the ventilated alveoli of the individual, wherein (1) the buffer is provided to the individual in the form of a powder, and (2) the individual is selected from the group consisting of a premature infant, a person receiving artificial respiration by a mechanical respirator, and a person who engages in an activity associated with inhalation of particulate matter.

19. The method of claim 18, wherein the individual is a smoker.

20. The method of claim 18, wherein the individual is a premature infant.

21. A method for treatment of an individual susceptible to a pulmonary condition involving insufficient secretion of surfactant by type II alveolar cells, said insufficiency being attributable to abnormally low pH of the aqueous film bathing the alveolar luminal surface of said cells, said method comprising causing an individual susceptible to said pulmonary condition to inhale an amount of a pH-raising buffer effective to maintain a normal rate of surfactant secretion by type II alveolar cells in the ventilated alveoli of said individual, wherein (1) the buffer is provided to the individual in the form of a solution that does not contain an alkylaryl polyether alcohol, and (2) the individual is selected from the group consisting of a premature infant, a person receiving artificial respiration by a mechanical respirator, and a person who engages in an activity associated with inhalation of particulate matter.

22. The method of claim 21, wherein the individual is a smoker.

23. The method of claim 21, wherein the individual is a premature infant.

24. A method for treatment of an individual susceptible to a pulmonary condition involving insufficient secretion of surfactant by type II alveolar cells, said insufficiency being attributable to abnormally low pH of the aqueous film bathing the alveolar luminal surface of said cells, said method comprising causing an individual susceptible to said pulmonary condition to inhale an amount of a pH-raising buffer effective to maintain a normal rate of surfactant secretion by type II alveolar cells in the ventilated alveoli of said individual, wherein (1) the buffer is provided to the patient in the form of a solution that, if the buffer is an alkali metal bicarbonate, contains at least 2.5% said buffer by weight; and (2) the individual is selected from the group consisting of a premature infant, a person receiving artificial respiration by a mechanical respirator, and a person who engages in an activity associated with inhalation of particulate matter.

25. The method of claim 24, wherein the individual is a smoker.

26. The method of claim 25, wherein the individual is a premature infant.

27. A method for treating a patient susceptible to or having the pulmonary symptoms of a condition selected from the group consisting of cystic fibrosis, bronchiectasis, bronchiolitis, emphysema, bronchial pneumonia, allergic bronchopneumonia, viral pneumonia, and encephalitis with retained secretions, said condition being attributable to abnormally low pH of the aqueous film bathing the alveolar luminal surface of type II alveolar cells, comprising identifying a patient susceptible to or having said condition, and causing said patient to inhale an amount of a pH-raising buffer effective to alleviate said symptoms, wherein the buffer is provided to the patient in the form of a powder.

28. The method of claim 27, wherein the buffer comprises bicarbonate ion.

29. The method of claim 27, wherein the buffer comprises PIS-TRIS propane, MOPS, HEPES, DIPSO, TAPSO, TRIZMA, HEPPSO, POPSO, EPPS, Tricine, Bicine, CAPS, dibasic sodium phosphate, dibasic potassium phosphate, or triethanolamine.

30. A method for treating a patient susceptible to or having the pulmonary symptoms of a condition selected from the group consisting of cystic fibrosis, bronchiectasis, bronchiolitis, emphysema, bronchial pneumonia, allergic bronchopneumonia, viral pneumonia, and encephalitis with retained secretions, said condition being attributable to abnormally low pH of the aqueous film bathing the alveolar luminal surface of type II alveolar cells, comprising identifying a patient susceptible to or having said condition, and causing said patient to inhale an amount of a pH-raising buffer effective to alleviate said symptoms, wherein the buffer is provided to the patient in the form of a solution that does not contain an alkylaryl polyether alcohol.

31. The method of claim 30, wherein the buffer comprises bicarbonate ion.

32. The method of claim 30, wherein the buffer comprises BIS-TRIS propane, MOPS, HEPES, DIPSO, TAPSO, TRIZMA, HEPPSO, POPSO, EPPS, Tricine, Bicine, CAPS, dibasic sodium phosphate, dibasic potassium phosphate, or triethanolamine.

33. A method for treating a patient susceptible to or having the pulmonary symptoms of a condition selected from the group consisting of cystic fibrosis, bronchiectasis, bronchiolitis, emphysema, bronchial pneumonia, allergic bronchopneumonia, viral pneumonia, and encephalitis with retained secretions, said condition being attributable to abnormally low pH of the aqueous film bathing the alveolar luminal surface of type II alveolar cells, comprising identifying a patient susceptible to or having said condition, and causing said patient to inhale an amount of a pH-raising buffer effective to alleviate said symptoms, wherein the buffer is provided to the patient in the form of a solution that, if the buffer is an alkali metal bicarbonate, contains at least 2.5% said buffer by weight.

34. The method of claim 33, wherein the buffer is inhaled as an aerosol of an aqueous solution.

35. The method of claim 33, wherein the buffer comprises bicarbonate ion.

36. The method of claim 33, wherein the buffer comprises BIS-TRIS propane, MOPS, HEPES, DIPSO, TAPSO, TRIZMA, HEPPSO, POPSO, EPPS, Tricine, Bicine, CAPS, dibasic sodium phosphate, dibasic potassium phosphate, or triethanolamine.

\* \* \* \* \*